United States Patent [19]

Faruk

[11] Patent Number: 5,239,090
[45] Date of Patent: Aug. 24, 1993

[54] CERTAIN OPTICALLY ACTIVE 3,4-DIHYDROBENZOPYRAN-4-OLS WHICH ARE INTERMEDIATES

[75] Inventor: Erol A. Faruk, Harlow, England
[73] Assignee: Beecham Group p.l.c., England
[21] Appl. No.: 840,405
[22] Filed: Feb. 24, 1992

Related U.S. Application Data

[62] Division of Ser. No. 472,012, Jan. 30, 1990, Pat. No. 5,126,460.

[30] Foreign Application Priority Data

Feb. 1, 1989 [GB] United Kingdom ............ 8902118

[51] Int. Cl.$^5$ ............ C07D 311/68; C07D 311/70; C07D 311/72
[52] U.S. Cl. ............................ 549/401; 549/336
[58] Field of Search ............................ 549/401, 336

[56] References Cited

FOREIGN PATENT DOCUMENTS

| | | |
|---|---|---|
| 0009912 | 4/1980 | European Pat. Off. |
| 076075 | 4/1983 | European Pat. Off. |
| 120428 | 10/1983 | European Pat. Off. |
| 093535 | 11/1983 | European Pat. Off. |
| 120426 | 10/1984 | European Pat. Off. |
| 126350 | 11/1984 | European Pat. Off. |
| 139992 | 5/1985 | European Pat. Off. |
| 260555 | 3/1988 | European Pat. Off. |
| 296975 | 12/1988 | European Pat. Off. |
| 2523281 | 12/1975 | Fed. Rep. of Germany. |
| 1548222 | 7/1979 | United Kingdom. |
| 2204868 | 11/1988 | United Kingdom. |

OTHER PUBLICATIONS

Paul Newman, *Optical Resolution Procedures For Chemical Compounds*, vol. 1, pp. 11, 246, 256, 47 (1979).
Ashwood, et al, "Synthesis and Antihypertensive Activity of 4-(Cyclic amido)-2H-1-benzopyrans", Journal of Medicinal Chemistry, 1986, vol. 29, No. 11, pp. 2195-2201.
Chemical Abstracts, vol. 109, No. 25, 1988, p. 389, Column 2, abstract-No. 230 805q.
Chemical Abstracts, vol. 99, No. 19, 1983, p. 595, column 2, abstract-No. 158 185t & J. Med. Chem. 1983, 26(11), 1582-9.
Chemical Abstracts, vol. 101, No. 11, 1984, p. 622, column 2, abstract-No. 90 726x & J. Med. Chem. 1984, 27(9), 1127-31.

*Primary Examiner*—Bernard Dentz
*Attorney, Agent, or Firm*—Rosenman & Colin

[57] ABSTRACT

The (3S,4R)-isomer of a compound of formula (E) is disclosed.

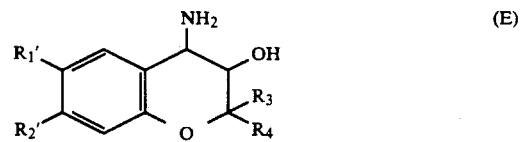

3 Claims, No Drawings

CERTAIN OPTICALLY ACTIVE 3,4-DIHYDROBENZOPYRAN-4-OLS WHICH ARE INTERMEDIATES

CROSS-REFERENCE

This is a division of Ser. No. 472,012 filed Jan. 30, 1990, U.S. Pat. No. 5,126,460.

The present invention relates to a process for the preparation of one isomeric form of chemical compounds having pharmacological activity.

EP-A-0076075 (Beecham Group p.l.c.) discloses a class of 3,4-dihydrobenzopyranols, and corresponding esters and ethers, with an oxo-pyrrolidinyl or oxo-piperidinyl substituent at the 4-position. These compounds are disclosed as having a blood pressure lowering activity.

EP-A-0120428 (Beecham Group p.l.c.) discloses that the (3S,4R)-isomer of the above compounds has greater blood pressure lowering activity than the (3R,4S)-isomer.

The compounds disclosed in EP-A-0120428 are of general formula (A):

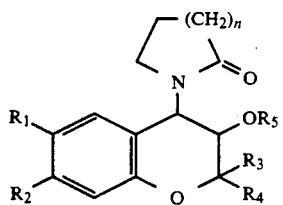

wherein
one of $R_1$ and $R_2$ is hydrogen and the other is selected from the class of alkylcarbonyl, alkoxycarbonyl, alkylcarbonyloxy, alkylhydroxymethyl, nitro, cyano, chloro, trifluoromethyl, alkylsulphinyl, alkylsulphonyl, alkoxysulphinyl, alkoxysulphonyl, alkylcarbonylamino, alkoxycarbonylamino or aminosulphinyl, aminosulphonyl or aminocarbonyl, the amino moiety being optionally substituted by one or two alkyl groups, or alkylsulphinylamino, alkylsulphonyl-amino, alkoxysulphinylamino or alkoxysulphonylamino or ethylenyl terminally substituted by alkylcarbonyl, nitro or cyano, or —C(alkyl)NOH or —C(alkyl)NNH$_2$, the alkyl groups or alkyl moieties of alkyl-containing groups having from 1 to 6 carbon atoms;

one of $R_3$ and $R_4$ is hydrogen or alkyl having from 1 to 4 carbon atoms and the other is alkyl having from 1 to 4 carbon atoms, or $R_3$ and $R_4$ together are $C_{2-5}$ polymethylene;

$R_5$ is hydrogen, alkyl having from 1 to 3 carbon atoms or acyl having from 1 to 8 carbon atoms; and n is 1 or 2.

The (3S,4R)-isomer of a compound of formula (A) is of formula (A'):

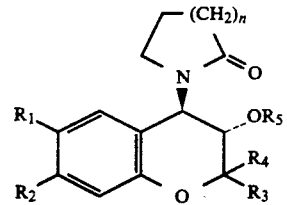

wherein the variables are as defined in formula (I).

The (3S,4R)-isomers of compounds of formula (A) have the same configuration as that enantiomer of a compound of formula (B) which has a negative optical rotation:

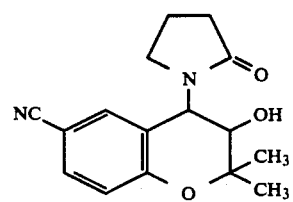

the OH and pyrrolidon-1-yl groups in formula (B) being mutually trans. The compound of formula (B) is trans-6-cyano-3,4-dihydro-2,2-dimethyl-4-(2-oxo-1-pyrrolidinyl)benzo[b]pyran-3-ol, also known as cromakalim, the (—)-isomer thereof, being known as lemakalim.

Also described in EP-A-0120428 is a resolution process for separating the (3S,4R)-isomer of compounds of formula (A) from a mixture with the (3S,4R)-isomer by fractional crystallisation, exemplified by a carbamate derivative obtained by reaction with (—)-α-methyl benzyl isocyanate.

In EP-A-0120428, in one procedure for obtaining a mixture of these isomers, the compound of formula (A) is obtained by cyclising a compound of formula (C) or formula (D):

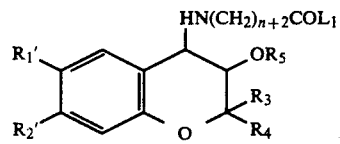

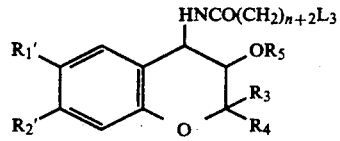

wherein $R_1'$, $R_2'$ are $R_1$ or $R_2$ or a group or atom convertible thereto, $R_1$ to $R_5$ and n are as hereinbefore defined and $L_1$ and $L_3$ are leaving groups, and wherein the substituted amino group is trans to the $OR_5$ group; where necessary converting $R_1'$ and/or $R_2'$ to $R_1$ and/or $R_2$; and optionally converting $R_5$ to another $R_5$ as hereinbefore defined.

The leaving group $L_1$ is a group that is displaceable by a secondary amino nucleophile. The leaving group $L_3$ is a group that is displaceable by a secondary amino nucleophile adjacent to a carbonyl function.

It has now been found that, while compounds of formula (A) are preferably formed by a procedure in which the pyrrolidonyl or piperidonyl ring is formed by cyclisation as a final step, it is advantageous to perform the resolution to isolate or concentrate the (3S,4R)-configuration before the cyclisation takes place.

Therefore in its broadest aspect the present invention provides a process for the preparation of a pure (3S,4R)-isomer of a compound of formula (A) in which the pyrrolidonyl or piperidonyl ring is formed by cyclising an appropriate precursor dihydrobenzopyranol compound that has already been resolved to the ((3S,4R)-configuration, or a mixture in which the (3S,4R)-configuration predominates with respect to the (3S,4R)-configuration.

Preferably the cyclisation is performed on a compound of formula (D) as defined above of the appropriate configuration. The leaving group $L_3$ is preferably chloro. The cyclisation can be carried out in a solvent in the presence of a base, for example dimethylformamide and sodium hydride, or ethanol or toluene and sodium methoxide. Alakli metal alcoholates such as potassium tert butoxide or sodium isopropoxide are also suitable bases.

Preferably the base is added to the compound to be cyclised while the latter is still in the solvent used during introduction of the cyclisable ligand, as described below. (i.e. the compound of formula (C) or (D) is used in situ).

Details of the cyclisation of the compound of formula (C) can be found in EP-A-0120428, together with procedures for its preparation.

The desired isomer or enriched isomer mixture of compounds of formula (C) and (D) can be obtained by resolution of a racemix mixture. Preferably they are obtained respectively by reaction of the corresponding aminoalcohol of formula (E):

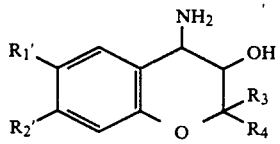

which is already in the desired enantiomeric configuration, with a compound of formula (F) or (G):

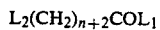 (F)

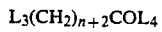 (G)

where $L_2$ is a leaving group that is displaceable by a primary amino nucleophile, and $L_4$ is a leaving group that, when adjacent to a carbonyl function, is displaceable by a primary amino nucleophile. Both may typically be chloro.

This reaction preferably takes place in a solvent to which the base required for promotion of cyclisation can be added directly. Suitable solvents include for example, N-methylpyrrolidone, dimethylformamide, dimethylpropylene urea, dimethylimidazolidone, tetrahydrofuran or other ethers, and toluene.

Further details of these procedures and alternative routes to a compound of formula (C) or (D) are given in EP-A-0120428.

The desired isomer of the compound of formula (E) is preferably obtained by fractional crystallisation of a suitable derivative. A suitable resolving agent is (+)-endo-3-bromocamphor-9-sulphinic acid as its ammonium salt. Other camphor sulphinic acids may also be used, or acids such as tartaric acids, substituted tartaric acids, mandelic acids and nitrotartranilic acids. Suitable solvents are lower (e.g. $C_{1-5}$) alcohols such as ethanol or propan-2-ol, possibly with added water. With some acids, polar organic solvents such as esters and ketones may be suitable.

A racemic mixture of the amino alcohol of formula (E) is preferably obtained by reaction of the corresponding epoxy compound of formula (H):

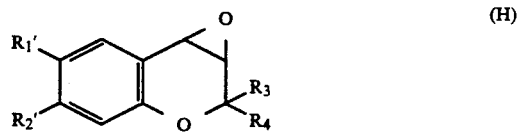 (H)

with ammonium hydroxide, in a lower alcohol, preferably a $C_{1-3}$ alkanol, such as propan-2-ol.

Alternative procedures for preparation of the amino alcohol can be found in EP-A-0120428, which also gives details of the preparation of the epoxy compound of formula (H).

After performing the cyclisation described above, other conversions may be carried out in the case where one of $R_1'$ or $R_2'$ is a group or atom convertible to the defined class of substituents for $R_1$ or $R_2$. Such conversions are generally well-known in the art. For example, a hydrogen atom may be replaced by a nitro group by nitrating in a known manner a compound, wherein one of $R_1'$ and $R_2'$ is hydrogen.

In the case where $R_1'$ or $R_2'$ is a group or atom convertible to hydrogen, such conversions are also generally well-known in the art. For example, the acetamido group may be replaced by a hydrogen atom by hydrolysins a compound wherein one of $R_1'$ and $R_2'$ is acetamido, converting the resulting amine into a diazonium salt, and finally decomposing it under reductive conditions.

Instead of carrying out the conversion of a group or atom $R_1'$ or $R_2'$ into hydrogen or into one of the class of substituents defined for the other of $R_1$ and $R_2$ after cyclising, it is greatly preferred that any such conversions are carried out at an earlier stage, preferably before the preparation of the epoxy compound of formula (H). In other words, it is preferred that, for the processes of the invention $R_1'$ and $R_2'$ are $R_1$ and $R_2$ respectively.

In the compounds described, one of $R_1$ and $R_2$ is hydrogen. The other is preferably selected from the class of alkylcarbonyl, alkoxycarbonyl, nitro or cyano, in particular nitro or cyano.

The alkyl groups or alkyl moieties or alkyl-containing groups, in respect of the other of $R_1$ and $R_2$, are preferably methyl or ethyl.

It is preferred that $R_2$ is hydrogen and $R_1$ is selected from the class of substituents as defined hereinbefore. It is particularly preferred that $R_2$ is hydrogen and $R_1$ is nitro or cyano. It is also preferred that $R_2$ is hydrogen and $R_1$ is acetyl.

It will be appreciated that $R_1$ and/or $R_2$ may also be selected from the values disclosed for the corresponding variables in EP-A-314446 (American Home Products Corporation), EP-A-29695 and 412432 (Sanofi,), EP-A-298452 (F. Hoffmann-La Roche and Co.), EP-A-273262, EP-A-308972 and 340718 (Merck Patent GmbH), EP-A-277611, EP-A-277612 and 337179 (Hoechst Aktiengesellschaft), EP-A-339562 (Yoshitomi Pharmaceutical Industries Ltd.), GB 2204868A (Sandoz Limited) and WO 89/07103 (Nissan Chemical Industries Ltd.).

$R_3$ and $R_4$ are preferably both alkyl having from 1 to 4 carbon atoms. In particular they are each methyl or ethyl, preferably each methyl.

When $R_5$ is alkyl, preferred examples thereof include methyl, ethyl and n-propyl, of which methyl is most preferred. When $R_5$ is acyl, a preferred class is unsubstituted carboxylic acyl, such as aliphatic acyl or benzoyl. $R_5$ however is preferably hydrogen.

Preferably, the (3S,4R)-isomer of a compound of formula (A) or an intermediate of formula (C), (D) or (E), is in a form containing from 0 to 40%, 0 to 30%, 0 to 20% or 0 to 10% of the corresponding (3S,4R)-isomer. More preferably, the (3S,4R)-isomer is in a form containing 0 to 5% of the corresponding (3S,4R)-isomer. Most preferably, the (3S,4R)-isomer is in a form containing 0% or no detectable amount of the corresponding (3S,4R)-isomer. All percentages hereinbefore are percentages of the mixture by weight. The presence of (3S,4R)-isomer may, for example, be routinely detected by the comparison of the optical rotation of a sample of the isomeric mixture with that of a pure sample of the (3S,4R)-isomer, or by the $^1$H nmr spectrum of a sample of the isomeric mixture in the presence of a chiral shift reagent or chiral solvating agent.

The term 'resolution' is used herein in the conventional practical sense used in the art to include partial resolution, that is, the separation of a mixture of enantiomers of a compound (in any ratio) into two fractions, one of which is enriched on one enantiomer relative to the initial mixture. Resolution may be effected conventionally by derivatising the mixture with a chiral derivatising agent, to form a mixture of diastereomers. The components of the mixture may then be separated conventionally, for example by fractional crystallization. Separation may be complete, or partial.

The absolute configuration of each isomer of a compound of formula (A), (C), (D) or (E), at the 3- and 4-centres may be conveniently be determined by routine and conventional X-ray crystallographic analysis of an isolated diastereomeric derivative of that isomer, the configuration at the 3- and 4-centres of the isomer and its derivative being the same. For example, an isomer of a compound of formula (A) wherein $R_5$ is H may be reacted with a chiral esterifying agent with retention of 3- and 4-centre configuration to form a diastereomeric ester derivative of the isomer. This may be isolated as a crystalline solid and the crystals used for the foregoing X-ray analysis. An isomer of a compound of formula (A) wherein $R_5$ is an alkyl or acyl group as hereinbefore defined may be converted conventionally to the corresponding isomer of a compound of formula (A) wherein $R_5$ is H, with retention of 3- and 4- centre configuration. This may then be derivatised and its absolute configuration determined as described hereinbefore.

The optical rotation of any similarly resolved and isolated enantiomer of any of the other compounds mentioned above may be routinely ascertained by conventional methods.

The (3S,4R)-isomer of a compound of formula (I) has abetter blood pressure lowering activity than the corresponding (3S,4R)-isomer. This isomer is therefore useful in the treatment of hypertension, optionally in admixture with the corresponding (3S,4R)-isomer as hereinbefore defined.

Details of suitable formulations may be found in EP-A-0120428.

Preferred embodiments of the pre-cyclisation resolution process of this invention are illustrated in the following Examples.

Alternative procedures for the cylisation are illustrated in Example 1; one involving different solvents for introduction of the cyclisable ligand and adding the base to promote cyclisation, the other using a common solvent for both procedures.

The preparation of the starting material in Example 1, ($\pm$)-trans-3-bromo-6-cyano-3,4-dihydro-2,2-dimethyl-4-hydroxy-2H-benzopyran is described in 'Description 1' in EP-A-0076075 in the name of Beecham Group p.l.c.

EXAMPLE 1

($\pm$)-trans-4-Amino-6-cyano-3,4-dihydro-2,2-dimethyl-2H-1-benzopyran-3-ol

Sodium hydride (80% dispersion in oil, 13.7 g) was added in portions over 1 h to a stirred solution of ($\pm$)-trans-3-bromo-6-cyano-3,4-dihydro-2,2-dimethyl-2H-benzopyran-4-ol (124.3 g) in tetrahydrofuran (250 ml) kept under a dry nitrogen atmosphere. The mixture was stirred for an additional 0.5 h after which a solution of the 3,4-epoxide resulted. Ethanol (620 ml) followed by 0.880 ammonium hydroxide (375 ml) were added, and the resulting mixture stirred at 60°-65° C. for 12 h before cooling to room temperature. The organic solvents were evaporated off and the aqueous residue acidified with 5N hydrochloric acid (125 ml). The mixture was then washed well with dichloromethane (total used=1.0 L) before basifying with 40% aq. sodium hydroxide (80 ml). It was then re-extracted with dichloromethane (4×250 ml) and the combined extracts washed once with brine and then dried ($Na_2SO_4$). Evaporation afforded the product as a gum which crystallised. This was broken up and triturated with a mixture of isopropyl ether and dichloromethane before filtering off and washing with further isopropyl ether. The product was dried under suction and finally under vacuum.

Yield: 83.5 g (87%) m.p. 116°-117° C.

$\delta$(CDCl$_3$): 1.21 (s, 3H); 1.51 (s, 3H); 2.10 (b, 3H); 3.30 (d, J=10 Hz, 1H); 3.65 (d, J=10 Hz, 1H), 6.82 (d, J=8 Hz, 1H); 7.42 (m, 1H) 7.74 (m, 1H)

Resolution of
($\pm$)-trans-4-Amino-6-cyano-3,4-dihydro-2,2-dimethyl-2H-1-benzopyran-3-ol The title compound (100 g) was dissolved in propan-2-ol (500 ml) with stirring and heating to 70° C. Water (250 ml) was added followed by (+)-ammonium 3-bromo-camphor-9-sulphonate (150.5 g). The mixture was stirred and warmed back to 70° C. to effect dissolution. 5N Hydrochloric acid (80 ml) was then added fairly rapidly until the mixture reached pH5. It was then cooled to 55° C. before seeding with authentic crystalline product. The mixture was cooled to room temperature before filtering off the product and washing with a mixture of isopropyl alcohol (50 ml) and water (25 ml). After drying in air at 50° C. the yield of 3-bromo-camphor-9-sulphonic acid salt of the (+)-isomer of the title compound was 75 g (31%).

$[\alpha]_D^{20}$ (C=1, MeOH)= +88.9°, m.p. 288°-291° C.

$\delta$(d$_6$-DMSO): 0.81 (s, 3H); 1.07 (s, 3H); 1.15 (s, 3H); 1.10-1.25 (m, 1H); 1.45 (s, 3H); 1.66-1.88 (m, 2H); 2.05-2.20 (m, 1H), 2.36 (d, J=14 Hz, 1H); 2.83 (d, J=14 Hz, 1H); 2.97 (ss, J=6,6 Hz, 1H); 3.64 (dd, J=6,10 Hz, 1H); 4.30 (d, J=10 Hz, 1H); 5.00 (d, J=6 Hz, 1H); 6.42 (d, J=6 Hz, 1H); 7.04 (d, J=8 Hz, 1H); 7.76 (m, 1H); 8.07 (bs, 1H); 8.53 (bs, 3H).

The foregoing salt (75 g) was dissolved in a solution of potassium hydroxide (10.3 g) in water (50 ml) and the mixture extracted with dichloromethane (4×250 ml). The combined extracts were washed once with brine and dried (Na$_2$SO$_4$). Evaporation afforded the (+)-isomer of the title compound as a glassy solid (30.5 g; 99%). Crystallisation from ethyl acetate-petrol afforded prisms of m.p. 85°–86° C.

$[\alpha]_D^{20}$ (C=1, MeOH)+82.4°.

(−)-trans-6-Cyano-3,4-dihydro-2,2-dimethyl-4-(2-oxo-1-pyrrolidinyl)-2H-1-benzopyran-3-ol Method A Triethylamine (7.95 g) was added to a stirred solution of (±)-trans-4-amino-6-cyano-3,4-dihydro-2,2-dimethyl-2H-1-benzopyran-3-ol (16.35 g) in dry tetrahydrofuran (40 ml) kept under a nitrogen atmosphere. The mixture was cooled to 15° C. and a solution of 4-cylorobutyryl chloride (11.45 g) in dry tetrahydrofuran (9 ml) added over 45 min while maintaining the reaction temperature at 15°–25° C. with external cooling.

After the addition was complete ethanol (82 ml) was added followed by sodium methoxide (16.2 g) in portions while constantly stirring. The mixture was then left to stir for 18 h at room temperature. Water (800 ml) was added to the stirred mixture in a steady stream to precipitate out the product. This was then filtered off and washed with water before drying. Crystallisation was carried out from refluxing ethyl acetate (1.1 L) with clarification through celite and concentrating down to a small volume to afford the title compound 16.8 g (78%).

$[\alpha]_D^{20}$ (C=1, CHCl$_3$)=−60.1°. m.p. 244°–252° C.

Method B

Triethylamine (10.85 g) was added to a stirred solution of (±)-trans-4-amino-6-cyano-3,4-dihydro-2,2-dimethyl-2H-1-benzopyran-3ol (21.8 g) in N-methyl pyrrolidone (100 ml) kept under a nitrogen atmosphere. The mixture was cooled to 5° C. and 4-chlorobutyryl chloride (15.15 g) added over 1 hour maintaining the reaction temperature below 20° C. with external cooling.

After a further 1 hour, potassium t-butoxide (36.15 g) was added in portions maintaining the reaction temperature below 30° C. The reaction mixture was stirred at room temperature for 2 hours then cooled at 10° C. and water (400 ml) added maintaining the temperature below 25° C. the precipitated product was collected by filtration, washed with water and dried. Crystallisation was carried out from refluxing ethyl acetate (1.5 l) with clarification through celite and concentration down to a small volume (140 ml) to afford the title compound 23.4 g (81.9%).

$[\alpha]_D^{20}$ (C=1, CHCl$_3$)=−58.5°. m.p. 247° C.

Method C

The 3-bromocamphor-9-sulphonate salt of (+)-trans-4-amino-6-cyano-3,4-dihydro-2,2-dimethyl-2H-1-benzopyrano-3-ol (211.6 g) was dissolved in a solution of sodium hydroxide (16.8 g) in water (710 ml) and the mixture extracted with dichloromethane (2×1060 ml). Evaporation afforded the free base which was dissolved in toluene (840 ml).

Triethylamine (42.7 g) was added to this stirred solution. The mixture was cooled to 5° C. and 4-chlorobutyrylchloride (59.6 g) added over 30 minutes maintaining the reaction temperature below 30° C. with external cooling.

After a further 1 hour, sodium methoxide (64.1 g) was added and the mixture was stirred for 2–3 hours at 30°–40° C. The reaction mixture was then cooled to 10° C. and water (1350 ml) added. The precipitated product was collected by filtration, washed with water and dried. Crystallisation was carried out from refluxing propan-2-ol (2.1 L) with clarification through celite and concentration down to a small volume (500 ml) to afford the title compound 97.8 g (86.8%).

$[\alpha]_D^{20}$ (C=1, MeOH)=−52.0°. m.p. 234°–236° C.

What is claimed is:

1. The (3S,4R)-isomer of a compound of Formula (E)

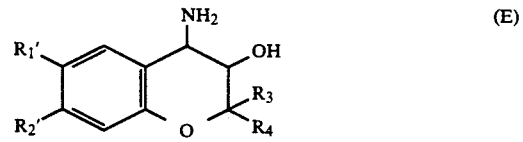

wherein the NH$_2$ and OH moieties are trans, and
wherein one of R$_1'$ and R$_2'$ is hydrogen and the other is selected from the group consisting of C$_{1-6}$ alkylcarbonyl, C$_{1-6}$alkoxycarbonyl, C$_{1-6}$alkylcarbonyloxy, C$_{1-6}$alkylhydroxymethyl, nitro, cyano, chloro, trifluoromethyl, C$_{1-6}$alkylsulphinyl, C$_{1-6}$alkylsulphonyl, C$_{1-6}$alkoxysulphinyl, C$_{1-6}$alkoxysulphonyl, C$_{1-6}$alkylcarbonylamino, C$_{1-6}$alkoxycarbonylamino or aminosulphinyl, aminosulphonyl or aminocarbonyl, the amino moiety being optionally substituted by one or two C$_{1-6}$alkyl groups, or C$_{1-6}$alkylsulphinylamino, C$_{1-6}$alkylsulphonylamino, C$_{1-6}$alkoxysulphinylamino or C$_{1-6}$alkoxysulphonylamino or ethylenyl terminally substituted by C$_{1-6}$alkylcarbonyl, nitro or cyano, or C$_{1-4}$(alkyl)NOH or C$_{1-4}$(alkyl)NNH$_2$, one of R$_3$ and R$_4$ is hydrogen or alkyl having from 1 to 4 carbon atoms and the other is alkyl having from 1 to 4 carbon atoms, or R$_3$ and R$_4$ together are C$_{2-5}$polymethylene;
optionally in admixture with up to 40% of the corresponding (3S,4R)-isomer.

2. The (3S,4R)-isomer according to claim 1, optionally in admixture with 0 to 5% of the corresponding (3S,4R)-isomer.

3. A (3S,4R)-isomer according to claim 1, which is (+)-trans-4-amino-6-cyano-3,4-dihydro-2,2-dimethyl-2H-1-benzopyran-3-ol.

* * * * *